United States Patent
Martinet et al.

[11] Patent Number: 5,860,266
[45] Date of Patent: Jan. 19, 1999

[54] METHOD AND MATERIALS FOR THE PROTECTION OF BUILDINGS AGAINST TERMITES

[75] Inventors: Pascal Martinet, les Roches de Condrieu; Olivier Lieux, Sorbiers; Guy Marcotte, Moidieu, all of France

[73] Assignee: Cecil S.A., France

[21] Appl. No.: 676,188

[22] PCT Filed: Dec. 28, 1994

[86] PCT No.: PCT/FR94/01541

§ 371 Date: Aug. 5, 1996

§ 102(e) Date: Aug. 5, 1996

[87] PCT Pub. No.: WO95/18532

PCT Pub. Date: Jul. 13, 1995

[30] Foreign Application Priority Data

Jan. 5, 1994 [FR] France .................................. 94 00179

[51] Int. Cl.⁶ .................................................. E04B 1/00
[52] U.S. Cl. ............................ 52/741.3; 43/124; 43/131; 43/132.1
[58] Field of Search ............................. 52/741.3; 43/124, 43/131, 132.1, 125; 428/98, 543, 907, 295.1, 295.4

[56] References Cited

U.S. PATENT DOCUMENTS

| | | | |
|---|---|---|---|
| 2,899,771 | 8/1959 | Burris, Jr. | |
| 3,931,692 | 1/1976 | Hermanson | 43/131 |
| 4,103,450 | 8/1978 | Whitcomb | 43/131 |
| 4,215,508 | 8/1980 | Allen et al. | 43/131 X |
| 4,793,474 | 12/1988 | Drake | 43/131 X |
| 5,094,028 | 3/1992 | Hume | 43/124 X |
| 5,224,288 | 7/1993 | Skelton et al. | |
| 5,233,787 | 8/1993 | Andersen | 43/132.1 |
| 5,359,806 | 11/1994 | Jeffery | 43/131 |

FOREIGN PATENT DOCUMENTS

| | | |
|---|---|---|
| 1568936 | 6/1980 | United Kingdom . |
| 2084021 | 4/1982 | United Kingdom . |
| WO 9014004 | 11/1990 | WIPO . |

OTHER PUBLICATIONS

Derwent Publication 84–124820.
Derwent Publ, 90–282545 & AU D 4,865,590 1990 (1 page).
Patent Abstracts of Japan No. JP5098717 Apr. 1993 (1 page).
Derwent No. 86–230350 (35) (1 page).
Derwent No. 88–194650 (28) (1 page).
JP63132803—880604 (1 page).
Derwent 86–164022 (26) 1 Page.
Derwent 87–233028 (33) 1 Page.
JP59062503—840410 (1 Page) Yakuhin, Insecticidal . . . Sheet.

*Primary Examiner*—Carl D. Friedman
*Assistant Examiner*—Beth Aubrey
*Attorney, Agent, or Firm*—Bierman, Muserlian and Lucas

[57] ABSTRACT

A method protecting building structures against termites comprising over the entire erection surface exposed by digging erection of the structure a non-porous film of plastic material impregnated throughout the film with a low concentration of an insecticide whereby the insecticide slowly diffuses.

11 Claims, 3 Drawing Sheets

METHOD AND MATERIALS FOR THE PROTECTION OF BUILDINGS AGAINST TERMITES

STATE OF THE ART

The present invention relates to the preventative protection of buildings against termites.

At present, the protection of buildings against the penetration of harmful isoptera (termites) is generally effected by pouring, spraying or injecting insecticide products in doses which should prove to be sufficient to ensure protection for a number of years. A ban on the use of certain insecticides, which are effective but which cause substantial toxic and ecotoxic pollution, has resulted in the use of substances which are less dangerous but which are less stable chemically, so that it is necessary for the operations to be repeated at more frequent intervals, which gives rise to difficult problems owing to the dispersal of undesirable materials into the environment.

Moreover, these preventative and curative renewal treatments are, by definition, carried out after the construction of tho building and, therefore, it is necessary to drill through the walls, floors, etc, which involves heavy and expensive work, causing inconvenience and the complete effectiveness of which is difficult to assure, since it is not always possible to drill the recommended number of holes. Furthermore, after construction, certain locations prove to be inaccessible to preventative and/or curative treatments of this type.

Finally, in an endeavour to increase the effectiveness of the preventative and/or curative treatments, there may be a considerable temptation to overdose the product, particularly around inaccessible locations, with the obvious dangers of pollution, which were precisely those which it was desired to avoid.

If it is recalled that it only requires one or more unprotected ways of penetration, which are very few in number, to allow the termites to invade a building and cause the well-known damage thereto, it is possible to judge the gravity of the problem and the necessarily serious deficiencies of the preventative and/or curative renewal treatments, even if they have been properly carried out, since the "chemical barrier" is rarely continuous.

DESCRIPTION OF THE INVENTION

The present invention aims to obviate these drawbacks and relates to a method for the protection of buildings against termites, which method is put into effect during the construction of the buildings themselves, and which is characterised in that said protection is permanent and complete, even though it makes use of new generation termicides, this combination of properties hitherto being considered to be impossible.

In fact, it was known how to obtain complete and permanent protection prior to construction but only by pouring, etc., substances which are now prohibited.

It was also known to use less powerful substances, however, this depended on the use of preventative and/or curative renewal treatments (therefore, the method was not "permanent") and gave rise to the very considerable danger of allowing the presence Of unprotected penetration paths (therefore, the method was not "complete").

However, the invention proposes a method and means combining four essential properties, the simultaneous combination of which was previously considered to be impossible:

1. Application prior to construction.
2. Use of new generation substances.
3. Completed treatment (continuous "chemical barrier", therefore no unprotected paths).
4. "Permanent" treatment (no need to resort to preventative retreatments or curative treatments in the event of failure).

Various plastic materials are also known for the controlled release of active ingredients. In particular, the document FR-A-3 491 037 (ROUSSEL-UCLAF) discloses packing and coating materials with insecticide properties and comprising a film of plastic material (polyethylene, for example) which is impregnated throughout by beans of a compound of the pyrethrin type.

The document JP 59-62503 discloses a kraft paper sheet impregnated with termicide and coated on one of its two sides with a plastic film. The product is supposed to diffuse through the polyethylene. It is a strong composite product intended for "under floor" use, i.e. in precise areas. Moreover, it involves old technology (1982), i.e. at a time when powerful termicides were authorised, even at high doses, parameters which are now strictly controlled.

U.S. Pat. No. 5,224,288 is also known, which is very significant in that it illustrates the state of the art immediately prior (1993) to the present invention. This American patent describes a fibrous mat impregnated with termicide. The fibres are mandatory, since only this arrangement ensures both a large surface area and adequate mechanical strength. Moreover, this document states that, necessarily, the mesh size of the fibrous structure has to be smaller than the insect, otherwise the insect can penetrate the structure.

Therefore, immediately prior to the present invention, the person skilled in the art understood:

that it was necessary to provide a large surface area to diffuse a sufficient amount of product;

that, despite this precaution, the insect could reach the fibrous mat and penetrate it, which shows that the chemical barrier was considered to be inadequate; perhaps, because of the "immediate" loss of product "by capillary attraction" into the ground.

Therefore, the person skilled in the art was not directed towards a solution of the film or fibrous mat type but was diverted away therefrom.

However, the invention relates to the application of an insecticidal plastic film for the protection of buildings against termites, using a method which comprises laying the film over the entire building surface exposed by the digging operations necessary for the erection of the building, including the foundation trenches, etc., this point being important, as will be explained below.

To judge the significance and originality of the invention it is necessary to view the situation in the context of the problem posed and its technical environment.

For example, within the framework of the aforementioned patent FR'037, it involved protecting the substances with an insecticide film. However, on the one hand, the application of the film could be mechanised and it was carried out in accordance with certain procedures and in the factory: therefore, correct application of the film was ensured and its insecticide action guaranteed. If a tear or fault was noticed, the packing could simply be diverted and repaired. Even it an undetected fault remained, it would result in only slight damage.

However, in the civil engineering sector it was unreasonable to expert building workers to apply a thin film very carefully to the ground and around the foundations, to check with even greater care that no reinforcing rods, pebbles, debris, etc., will perforate the film (it should be remembered that termite colonies are in a state of perpetual expansion and that their instinct urges them to radiate about the termitarium—they find the damp and "quiet" earth beneath a building to be particularly suitable—and to spread, preferentially, along pipe systems, etc., and that, therefore, a single unprotected passage is sufficient for an invasion of termites), to dispose carefully and with caution of the filters and building materials, cement, etc., so that these materials do not in turn perforate the film, namely to ask workmen to give up their practices associated with their technical sector and which are thus quite understandable.

This was all the more unlikely since passages have to be provided, particularly in the foundations, for the advance of pipe systems, cables, etc., of all types, which makes it necessary for the film to be perforated, cut, etc.

Finally, a film with controlled release of termicidal product could, by definition, only release small doses of product per unit of time, as confirmed by the aforementioned U.S. Pat. No. '288; therefore, at the very best one could expect a more or less repellent effect at the locations where the film has not been torn, perforated or badly positioned, or opened to pipe systems, etc., an effect which would thus quite simply direct the insects towards the locations at which there is a tear, perforation, etc., where they could penetrate the building without causing damage and, obviously, invade it.

Therfore, it was obvious to the person skilled in the art that a plastic film with controlled release could not provide any guarantee of success, taking into account the trade under consideration and its unavoidable constraints.

Accordingly, the trade has adapted to the drawbacks or curative treatments.

The Applicants, to their credit, have overcome the prejudices associated with the depositing of a film and have decided on a research programme, despite the investment involved and the almost certain risk of failure, that is according to the reasoning of professionals.

It is also to credit of the Applicants and their invention that they persevered after encountering the expected difficulties and, nevertheless, developed all the components of an original test programme and, finally, demonstrated that, contrary to all expectations, the termicidal film provides the desired solution.

The accompanying drawings, illustrated by way of example, will enable the invention, its features and the advantages which it can provide to be understood more clearly:

BRIEF DESCRIPTION OF THE DRAWINGS

FIG. 1 shows that, in an excavation formed after the digging work intended for the construction of the foundations (in chain lines) for a building, there has been spread out a series of sheets 1 of a film of plastic material impregnated with an insecticide product. These sheets 1 overlap one another (2) and they cover all the building surface, even extending substantially at ground level (3).

FIG. 2 shows what happens in practice. Some of the sheets are poorly positioned for covering purposes (no or insufficient overlapping), as shown at (9). Pebbles or debris perforate the film. During the laying operation grids, reinforcing rods (6) and projections perforate the film. During the casting of the foundations, the film is deflected or stretched under the pressure of the cast material m and the danger of piercing occurs at those locations where there is a sharp edge, as showing at (4), under the film or at the numerous locations where there is a void under the film (it is obvious that the film does not closely conform to well-prepared ground; it can only be placed on ground irregularly littered with debris and, accidentally, with metal parts, etc.), as shown at (8). In any case, the film has to be deliberately perforated to allow the passage of pipe systems or sheaths (7).

Each of these incidents creates a slit, opening or tour (5), many of which are unpredictable and cannot even be recognised, and only one of these slits, openings or tears is required to allow an invasion by termites.

Figure 1:
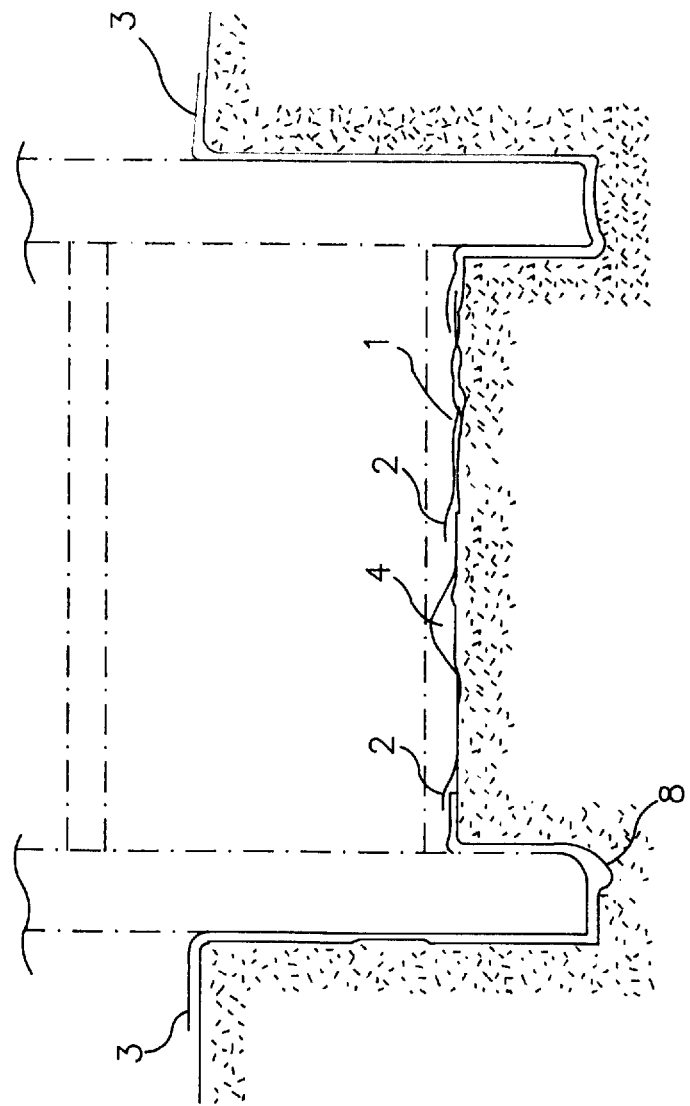
FIG. 1 of the drawings is a vertical schematic section showing the theoretical application of the system for protection against termites according to the invention.
Figure 2:
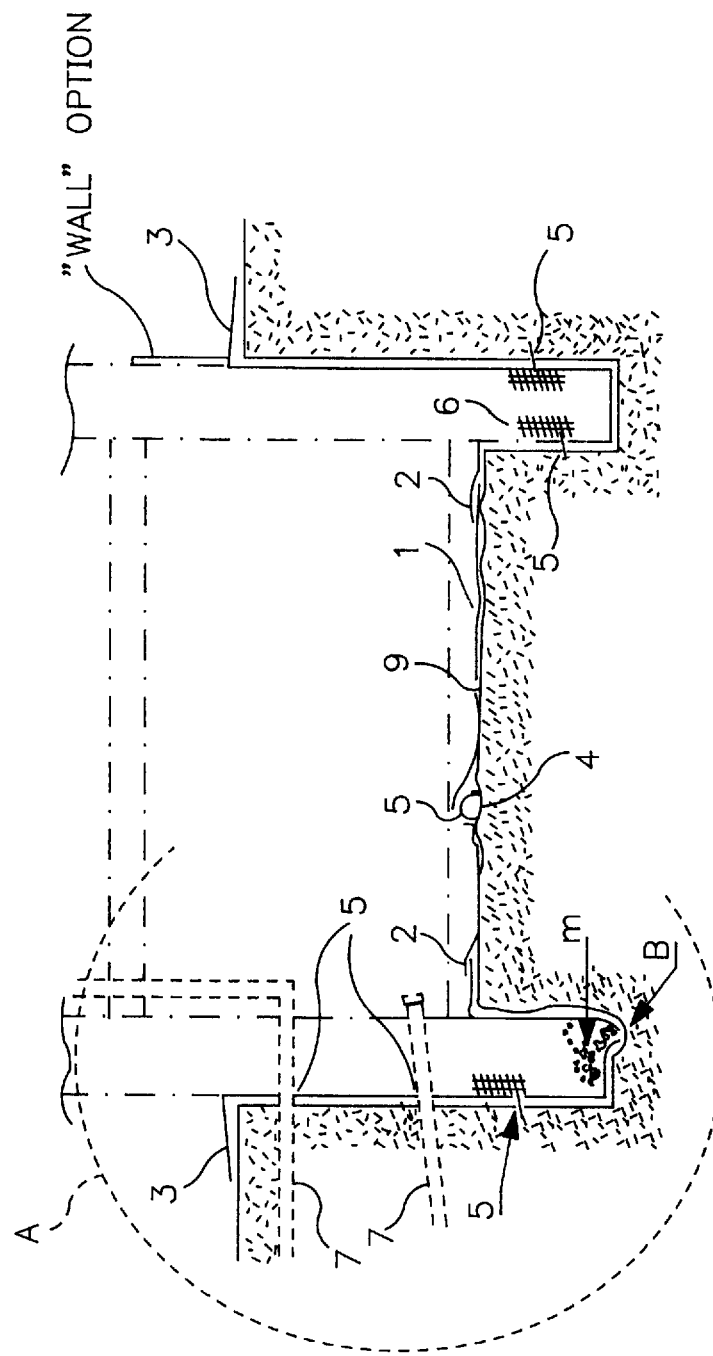
FIG. 2 is comparable to FIG. 1, except that it represents the actual application with serious incidents (tears, perforations, sheets laid with insufficient covering, etc.) which the person skilled in the art expected and which are in fact encountered.

Therefore, the problem posed is to attain the "zero fault", in this case the "zero penetration point". FIG. 2 shows the gamble which this objective represents with the simple aim of laying a film.

The invention lies in the manner in which it tackles the problem. There are two categories of tearing risks.

a) deliberate openings, such as those provided for the sheaths (7). These at least have the merit of being known. Therefore, one could think of effecting local treatment of the tear by sealing, etc. but in this field there would not be a total guarantee;

b) totally unpredictable accidental tears. No preventative measures are possible against the latter.

It was also known that, by definition, the film could not release a substantial amount of product when the release is gradual, and that the film and its vicinity are subjected to washing effects by water and moisture and other product losses, as confirmed by the above-mentioned U.S. Pat. No. '288. Finally, termicides are degraded at the very alkaline pH values of the building materials.

Therefore, tears could not be prevented and the product released could be relied upon to form a sufficiently concentrated and extensive barrier to the neutralise the tear zones.

Nevertheless, the Applicants decided to verify this latter point and found that, contrary to all expectations, the film treated against termites (described below) was able, despite the gradual release of small doses, to create 1) a repellent effect and 2) a contact and "shock" effect.

The unexpected contact effect observed is essential. According to the tests carried out, an insect arriving in the immediate vicinity of the film is clearly disturbed after only 10 s exposure: difficulty in moving, disturbed orientation and similarly disturbed behaviour. This is wholly in contrast with the teaching of U.S. Pat. No. '228.

Therefore, without being able to escape, the insect reaches the equally vary short period of time, at the end of which the lethal shock effect occurs.

In the extremely general case in which the insect is thus faced with a sound film, it is either repelled or subjected to the contact effect then to the shock effect. In the first case, it may seek and find a less protected opening. However, in this case, the Applicants have established that, contrary to expectations and knowledge, the insect is then subjected very rapidly (in only a few seconds!) to the contact effect which leads to the shock effect.

Figure 3:
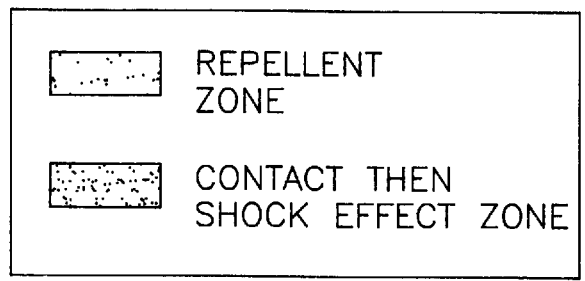
FIG. 3 represents an enlargement of a Zone A in FIG. 2, and also the detailed means of the invention and its effects.
Figure 3:
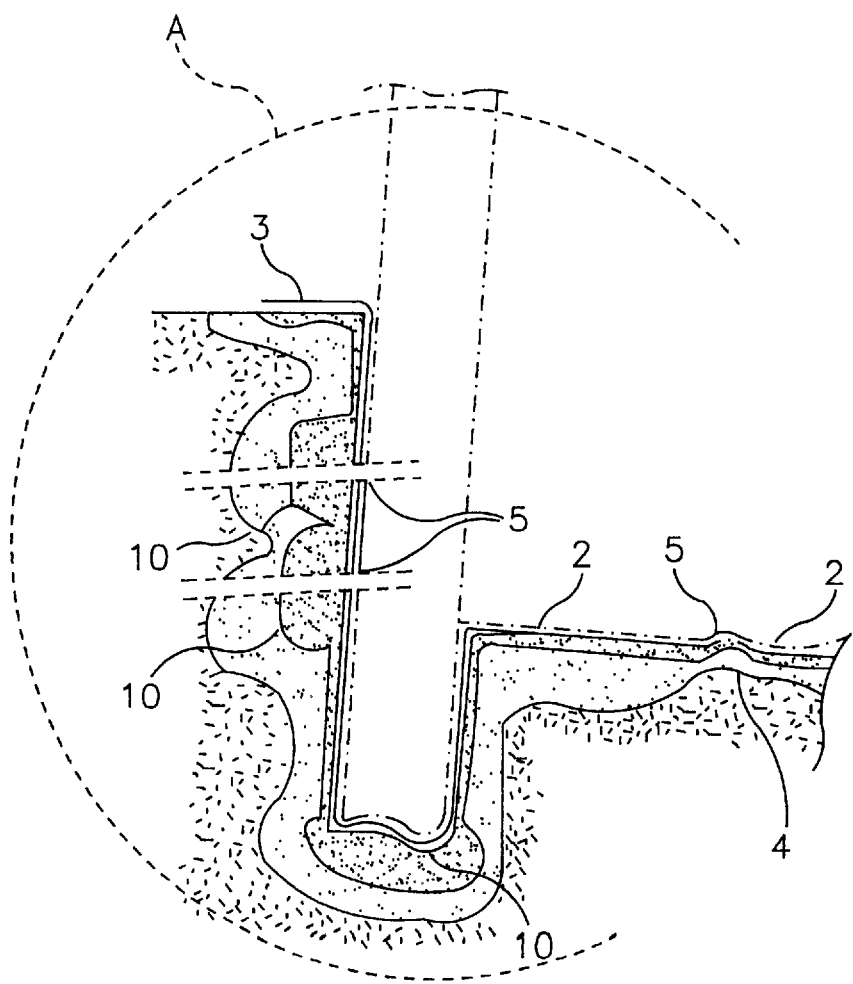

Therefore, the Applicants have established that even with not very careful installation practice, a termicidal film provides complete and permanent protection as a result of a double barrier illustrated in FIG. 3 having a repellent affect (protection of openings) and a contact and chock effect (destruction).

The plastic material film which forms the sheets 1 can be obtained by the extrusion of polymers, particularly polyolefins, such as polyethylene or polypropylene or polyvinyl chloride and analogous (co)polymers, the thickness of which is between 50 $\mu$m and 300 $\mu$m. The insecticide is incorporated in the plastic material during the production of the compound, the proportion being a function of the effectiveness or the active ingredient used. The production of the film is carried out starting from this compound by hot extrusion-blowing or by extrusion, it being possible for either one of these extrusion methods to be followed, optionally, by hot-pressing and analogous processes known to the person skilled in the art.

The insecticides which can be used are variable and are those known to the person skilled in the art. In particular, it is possible to use:

either insecticides of the chemical family of the pyrethrins of the type described in above-mentioned document ROUSSEL-UCLAF (permethrin or phenoxy-3 benzyl (±) Cis trans (dichloro 2,2 vinyl)-3 dimethyl-2,2 cyclopropane carboxylate with the molecular formula $C_{21}H_{20}Cl_2O_3$;

or insecticides of the chemical family of the carbamates, such as Benfuracarbe (dihydro-2,3 dimethyl-2,2 benzofuranyl-7N-(N-ethoxycarbonyl)-2 ethyl-N ispropylaminosulplienyl)-N-methylcarbonate), with the molecular formula $C_{20}H_{20}N_2O_5S$;

or organohalogens;

or organophosphorous compounds;

and known analogous products which need not be specified here.

The person skilled in the art will naturally be able to choose the most suitable and these examples are not restrictive. It would also be possible to use mixtures.

As is evident, openings necessarily have to be made in the film formed by the sheets 1, in particular for the passage of supply lines (water, gas, electricity) and outlet ducts. To obviate thie slightest risk and to be absolutely sure of restoring the continuous nature or the protective barrier formed by the plastic film, a preferred embodiment of the invention lies in treating these openings during the filling operation (of the foundation, for example) by incorporating into the substrate (11), which forms the covering filler, granules (10) of insecticidal plastic material, advantageously at a rate of (about) 1 volume of granules per 9 volumes of substrate. The openings have to be filled with this mixture over a thickness and a depth of at least about 10 cm The granules used have prererably (depending on the nature of the ground, on the degree of washing with water, and on the estimation of the dose released, factors which the person skilled in the art could readily determine by routine tests from reading the following examples and tables) dimensions of the order of about 2 to 3 mm in diameter over a length of about 2–5 mm. Their chemical composition is similar to that of the film which forms the sheets 1. They may also be waste from the production of the film or rejected pieces of film, etc., and the like but this is not preferred (problems in respect of homogeneity of the doses released). As a precaution, one could proceed in the same way at the locations where the film is most exposed to probable tearing, as at (8). Preference is given to granules and all geometries have roughness or sharp edges, such as cut rods.

The great advantage of this variant is two-fold: it is easily carried out by the building workers, with no particular care needed; and the preferred use of waste, etc., from the film.

The masonry work can be resumed after these simple operations.

The secondary advantages achieved by this method for protection against termites in relation to conventional systems for pouring insecticide compounds in the liquid phase are also obvious.

The active insecticide materials are protected from external attach by the plastic material of the film in which they are incorporated, said film allowing slow diffusion.

The quantities of insecticide products are very clearly lower than those used according to a conventional process. The following tables and examples allow a simple comparison to be made.

The risk of pollution to the ground and phreatic strata is greatly reduced sines the insecticides held captive within the plastic material are released only at a very low rate.

The danger of contamination of the environment in the event of an accident occurring during the conveyance of the insecticide film is absolutely zero, whereas there is a high danger associated with the conveyance of liquid insecticides to be poured.

The protective barrier formed by the sheets 1 is especially visible during complementary digging work, so that it can be easily restored.

This protective barrier can be easily removed in the event ot demolition.

The following tests have been carried out by the Applicants:

a) Study of the insecticide activity on Reticulitermes santonensis of a polyethylene film treated with permethrin.

Several polyethylene films are used having a thickness of 200 $\mu$m and containing different amounts of permethrin. These films were obtained using the method described above. A control film of polyethylene is also used which does not contain any biocidal active material.

The film to be tested is retained between 2 glass tubes which are open at the end, have an inner diameter of 50 mm and a height of 50 mm (S=19.63 cm2). A support of neutral material of 1 mm thickness is deposited on the surface of the film and supports a disc of filter paper which is moistened to saturation. The filter paper, which is thus not in contact with the treated film, serves after daily remoistening as nourishment and as water reserve for the insects required for the experiment. After the introduction into each of the devices of 25 Reticulitermes santongnsis workers in a good state of health, a cover of polyurethane foam is placed on each of the devices. The mortality rate is verified after 6 hours, 12 hours, 24 hours and then each day for 7 days, starting from the date when the insects were introduced into the experimental devices. For each concentration of biocide in the plastic material there were carried out two repeats of the test which, itself, uses four experimental devices of 25 termites per concentration.

The following table summarises the experimental results obtained.

Plastic material: polyethylene Active biocidal material: permethrin

| Dose of biocide in (m/m) in the support | % of mortality | | | | | | |
|---|---|---|---|---|---|---|---|
| | 6 H | 12 H | 24 H | 2 D | 3 D | 4 D | 7 D |
| 0.005 | 0 | 0 | 4 | 36 | 52 | 64 | 84 |
| 0.05 | 0 | 0 | 8 | 60 | 88 | 96 | 100 |
| 0.25 | 20 | 36 | 84 | 100 | | | |
| 0.50 | 52 | 88 | 100 | | | | |
| 1.00 | 100 | | | | | | |
| Controls | 0 | 0 | 0 | 0 | 0 | 2 | 8 |

CONCLUSIONS:

With a dose of 1% of purmethrin incorporated into the polyethylene the material exhibits satisfactory anti-termite characteristics.

b) Study of the insecticide activity on Reticulitermes santonensis of a polyethylene film treated with Benfuracarbe.

The test methodology is the same as that indicated in the foregoing; the films are obtained in accordance with the process described above.

The following table summarises the experimental results obtained.

| Dose of biocide in % (m/m) in the support | % of mortality | | | | | | |
|---|---|---|---|---|---|---|---|
| | 6 H | 12 H | 24 H | 2 D | 3 D | 4 D | 7 D |
| 0.005 | 0 | 0 | 0 | 4 | 12 | 20 | 65 |
| 0.05 | 50 | 64 | 100 | | | | |
| 0.25 | 100 | | | | | | |
| 0.50 | 100 | | | | | | |
| 1.00 | 100 | | | | | | |
| Controls | 0 | 0 | 0 | 0 | 0 | 2 | 8 |

CONCLUSIONS:

With a dose of 1% of benfuracarbe incorporated into the polyethylene the material exhibits satisfactory anti-termite characteristics.

b) Study of the influence of dilution by infiltrating water on the insecticide activity or the plastic material used by the method forming the subject-matter of the invention.

Samples of films treated as described above are held captive in the polyurethane foam. They are introduced vertically into the glass tube of a diameter of 50 mm and a height of 50 mm, at a rate of 4 samples per tube, treated with the same doses and with the same active principle. A device for dispensing liquid drop by drop is installed at the top of this experimental device. By means of the aforementioned device 8 liters of demineralised water are allowed to percolate through the foam supporting the films over a period of 48 hours and a rate of 40 drops per minute. This quantity of water represents, in relation to the experimental surface area, the approximate average of rain received in 5 years per square meter in various West European towns commonly recognised as being subject to termite invasion.

Following this dilution test, the films are removed from the devices and dried without being wiped. The insecticide activity is then verified according to the method described in paragraph a) above.

The following table summarises the experimental results obtained.

Plastic mterial: polyothylene

| Nature of biocide | Dose of biocide in % (m/m) in the support | % of morality | | | | | | |
|---|---|---|---|---|---|---|---|---|
| | | 6 H | 12 H | 24 H | 2 D | 3 D | 4 D | 7 D |
| Permethrin | 0.05 | 0 | 0 | 0 | 8 | 8 | 11 | 32 |
| | 0.25 | 0 | 0 | 13 | 37 | 69 | 100 | |
| | 0.50 | 30 | 56 | 72 | 90 | 100 | | |
| | 1.00 | 100 | | | | | | |
| Benfuracarbe | 0.05 | 0 | 0 | 0 | 36 | 49 | 78 | 94 |
| | 0.25 | 0 | 0 | 2 | 46 | 71 | 99 | 100 |
| | 0.50 | 16 | 24 | 30 | 68 | 100 | | |
| | 1.00 | 31 | 44 | 52 | 100 | | | |
| Treated controls | | 0 | 1 | 1 | 1 | 1 | 1 | 4 |

CONCLUSIONS:

With a dose or 1% of permethrin or benfuracarbe incorporated into the polyethylene the material exhibits satisfactory anti-termite characteristics after undergoing the dilution test.

d) Study of the insecticide activity on Reticulitermes santonensis of particles of polyethylene treated with different biocides, mixed with a substrate.

Particles of the following dimensions: diameter 2.5 mm, length 4 mm, obtained according to the above-described method, are incorporated into moistened Fontainebleau sand (1 volume of water per 4 volumes of sand) at a rate of 1 volume of granules per 9 volumes of sand. This properly homogenised mixture entirely fills a glass tube which is 50 mm in diameter and 350 mm in height. Fitted to the base of this tube is another glass cylinder, 50 mm in diameter and 50 mm in height, which is filled with moist sand containing a block of wood as bait. Care is taken to interpose between the two tubes a membrane of filter paper which will serve as a control passage. The device is covered by another glass tube (50 mm in diameter and 50 mm in height) containing a disc of polyurethane foam conforming to the inner diameter of the tube, and 25 mm in thickness. This disc is traversed by two holes 3 mm in diameter and a piece of wood, which originates from the breeding of Reticulitermes santonensis, is inserted into the centre of its upper surface. A population of Reticulitermes santonensis workers in a good state of health is introduced through the upper opening of the experimental device which is finally covered with a lid out into the polyurethane foam.

The depth of penetration into the treated substrate and the mortality rate are checked at the end of the 4-week test period. 4 experimental devices were used for each biocide tested and at each of the concentrations of biocide in the plastic material. Each of the tests was repeated twice. During each repetition 4 devices devoid of any biocide were used as controls.

The followlng table summarises the experimental results obtained.

| Nature of biocide | Dose of biocide in % (m/m) in the granules | Depth of penetration in the substrate in mm | Survival rate of termites |
|---|---|---|---|
| Permethrin | 0.25 | 150 | 18.00% |
| | 1.00 | 10 | 8.00% |
| Benfuracarbe | 0.25 | 199 | 11.4% |
| | 1.00 | 16 | 8.4% |
| Treated controls | | 400 | 80.8% |

CONCLUSIONS:

With a dose of 1% of permethrin or benfuracarbe incorporated into the polyethylene particles, the material, which is mixed with sana in the proportions defined above, imparts satisfactory anti-termite characteristics to the substrate.

These tests demonstrate the activity of the film laden with 1%, as well as the granules (10) which may be used mixed with the filler (11), and also the satisfactory resistance to dilution.

It was noted that the repellent etfect was effective practically whatever the dose applied.

The person skilled in the art will readily know how to determine the doses required for the "contact" and "shock" effects described according to the invention by routine tests based on the above examples and simple soil samples, etc.

The impregnation dose could be as low as about 0.5%, the upper limit being dictated by economic and standardisation criteria, for example about 2%, preferably 1%.

Moreover, it should be understood that the foregoing description has only been made by way of example and that it in no way restricts the scope of the invention, and replacing the described details ot the embodiments with any others which are equivalent will not represent any departure therefrom.

In particular, the film could be mounted a dozen centimeters along a wall, above the ground. It would also be possible to develop more or less vertical barriers arranged at a certain distance all around the location to be protected, over a suitable depth known by the person skilled in the dart.

A film according to the invention is disposed vertically in a trench protecting at any distance desired the entire periphery of the zone in question, the locations particularly under threat being filled optionally with the addition of granules according to the invention. It would also be possible merely to dig a trench and fill it with the addition of granules according to the invention. New works can thus be better protected and/or "renewing" treatments can be carried out in combination with or in replacement of the old method.

We claim:

1. A protective sheet comprising a porous film of plastic material impregnated throughout the film with a concentration of an insecticide of less than two percent, whereby the insecticide slowly diffuses.

2. A method of protecting building structures against termites comprising laying over the entire erection surface exposed by digging prior to erection of the structure the sheet of claim 1.

3. The method of claim 2 wherein the film is formed by a series of overlapping (2) sheets (1) protruding slightly outwardly at ground level (3).

4. The method of claim 2 wherein the plastic material is selected from the group consisting of polyethylene, polypropylene and polyvinyl chloride.

5. The method of claim 2 wherein the insecticide is a termicide selected from the consisting of pyrethrins, carbamates, organohalogens and organophosphorus compounds.

6. The method of claim 5 wherein the termicide is selected from the group consisting of permethrin and benfuracarbe.

7. The method of claim 2 wherein the plastic material is polyethylene and the insecticide is permethrin.

8. The method of claim 7 wherein the film is polyethylene containing 0.5 to 2% by weight of permethrin.

9. A method of protecting a building structure from termites comprising spreading, over at least a portion of the building structure exposed by digging, a mixture of a substrate of normal filler and granules of plastic material impregnated with insecticide and laying over the mixture the sheet of claim 1.

10. The method of claim 9 wherein the granules and the film are made of the same plastic material.

11. A building structure protected by the method of claim 2.

* * * * *